US00PP25070P3

(12) United States Plant Patent
Leis et al.

(10) Patent No.: US PP25,070 P3
(45) Date of Patent: Nov. 18, 2014

(54) STRAWBERRY PLANT NAMED 'MURANO'

(50) Latin Name: *Fragaria Ananassa×Duch.*
Varietal Denomination: MURANO

(71) Applicant: C.I.V.—Consorzio Italiano Vivaisti—Società Consortile A R.L., Comacchio FE (IT)

(72) Inventors: Michelangelo Leis, Ferrara (IT); Alessio Martinelli, Ferrara (IT)

(73) Assignee: C.I.V.—Consorzio Italiano Vivaisti—Societá Consortile A R.L., Comacchio FE (IT)

( * ) Notice: Subject to any disclaimer, the term of this patent is extended or adjusted under 35 U.S.C. 154(b) by 0 days.

(21) Appl. No.: 13/694,935

(22) Filed: Jan. 22, 2013

(65) Prior Publication Data

US 2014/0047598 P1 Feb. 13, 2014

(30) Foreign Application Priority Data

Aug. 9, 2012 (QZ) ..... PBR 20121731

(51) Int. Cl.
*A01H 5/00* (2006.01)

(52) U.S. Cl.
USPC ..... Plt./209

(58) Field of Classification Search
USPC ..... Plt./209
See application file for complete search history.

*Primary Examiner* — Anne Grunberg
(74) *Attorney, Agent, or Firm* — Foley & Lardner LLP

(57) ABSTRACT

A new and distinct variety of *Fragaria* L.. named 'MURANO', characterized by the description herein.

4 Drawing Sheets

Latin name of the genus and species claimed: *Fragaria Ananassa×Duch.*

Variety denomination: 'MURANO'.

CROSS REFERENCE TO RELATED APPLICATIONS

This application claims priority under 35 U.S.C. §119(f) of the Community plant variety office (CPVO) application No. 2012/1731 filed Aug. 9, 2012.

BACKGROUND OF THE INVENTION

The present invention relates to a new and distinct strawberry variety named 'MURANO', which was the result of a controlled cross performed in 2004 between the proprietary unpatented selection of Consorzio Italiano Vivaisti named 'R6R1-26' and a proprietary unpatented selection of Consorzio Italiano Vivaisti named 'A030-12'.

The progeny was first asexually propagated by stolons in S. Giuseppe di Comacchio Ferrara, Italy, in 2005.

The 'MURANO' variety was tested over the next several years in different European areas with high chill conditions. The tests started in 2006 and continued until 2011.

BRIEF SUMMARY OF THE INVENTION

Plants of the new Strawberry variety 'MURANO' can be distinguished from plants of the comparison Strawberry variety 'CIVRI-30' (Registered, CPVO Grant No. 14561) by the following unique combination of characteristics described in Table 1:

TABLE 1

| Comparison with Comparison Variety | | | |
|---|---|---|---|
| Denomination of similar variety | Characteristic in which the similar variety is different | State of expression of similar variety | State of expression of candidate variety |
| CIVRI-30 | Plant Vigor<br>Firmness | Medium-Weak<br>Firm | Medium-High<br>Very Firm |

Plants of the new Strawberry variety 'MURANO' can be distinguished from plants of the parent varieties 'A030-12' and 'R6R1-26' by the following unique combination of characteristics described in Table 2:

TABLE 2

| Comparison with Parent Varieties | | | |
|---|---|---|---|
| Characteristic in which the variety is different | State of expression of candidate variety | The female parent ('A030-12') | The male parent ('R6R1-26') |
| Plant vigor | Medium-high | Strong | Weak |
| Fruit color | Orange red to medium red | Dark red | Orange red |
| Fruit shape | Conical | Conical elongated | Globose |
| Fruit size | Large | Very large | Small to medium |
| Firmness | Very firm | Medium to firm | Firm |

Asexual reproduction of this new variety by stolons shows that the foregoing and all other characteristics and distinctions come true to form and are established and transmitted through succeeding propagations. The new variety reproduces true to type.

BRIEF DESCRIPTION OF THE PHOTOGRAPHS

The accompanying photographs illustrate the overall appearance of the new Strawberry 'MURANO' showing the colors as true as is reasonably possible with colored reproductions of this type. Colors in the photographs may differ slightly from the color value cited in the detailed botanical description, which accurately describe the color of 'MURANO'.

Figure 1:
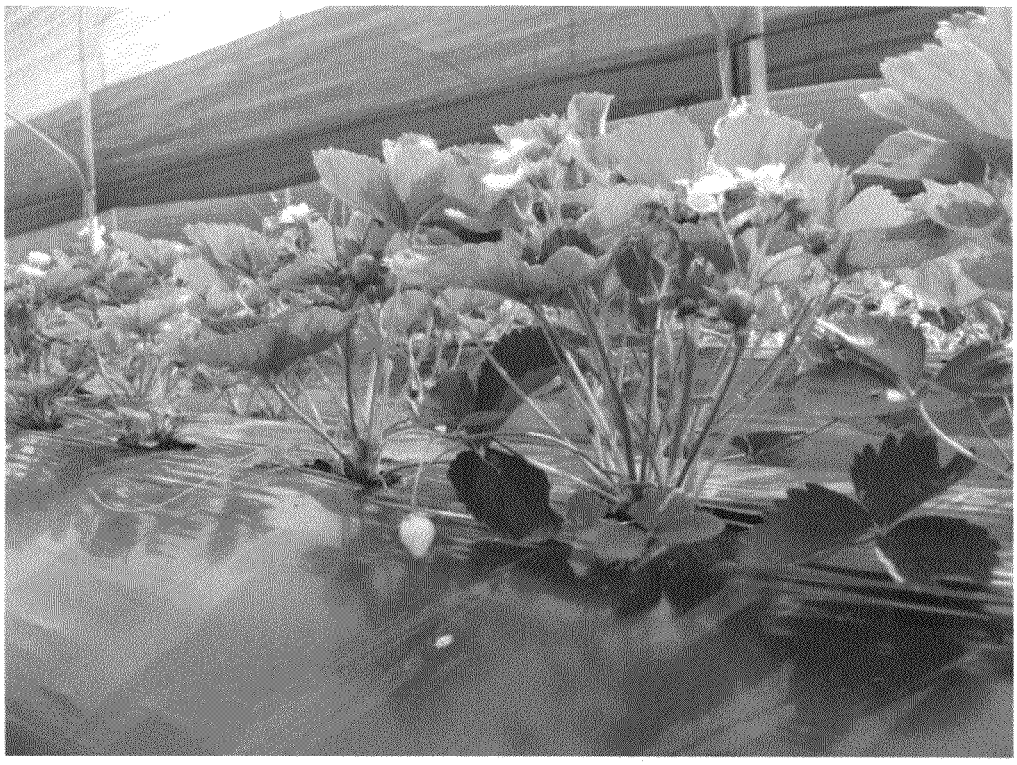
FIG. 1 shows the plant of 'MURANO'.
Figure 2:
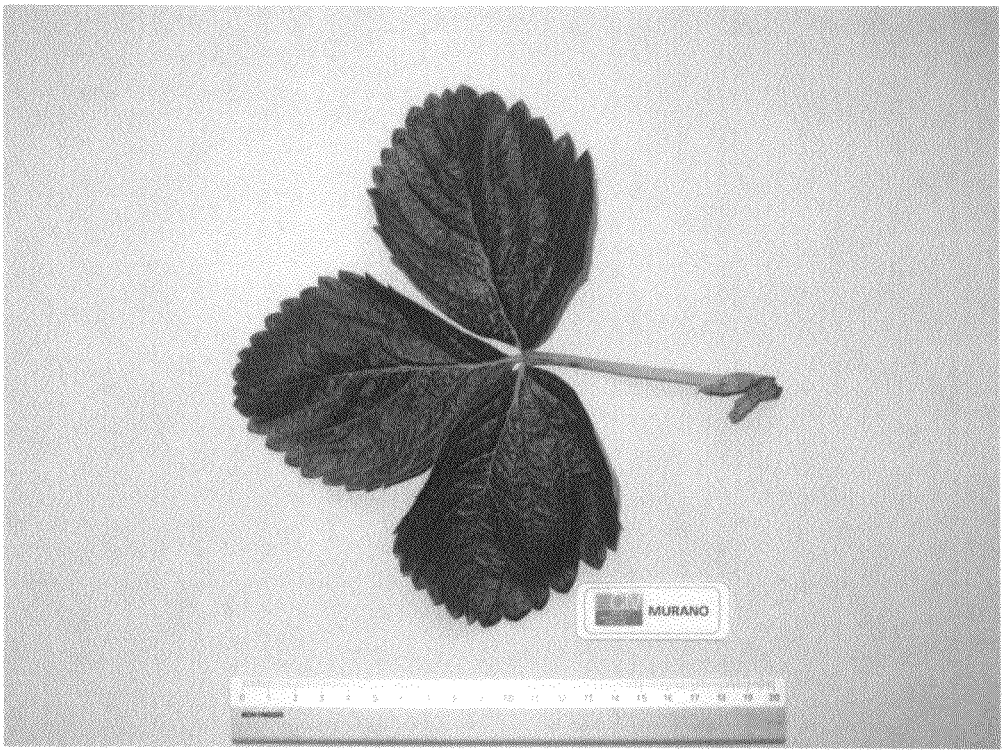
FIG. 2 shows the leaves of 'MURANO'.
Figure 3:
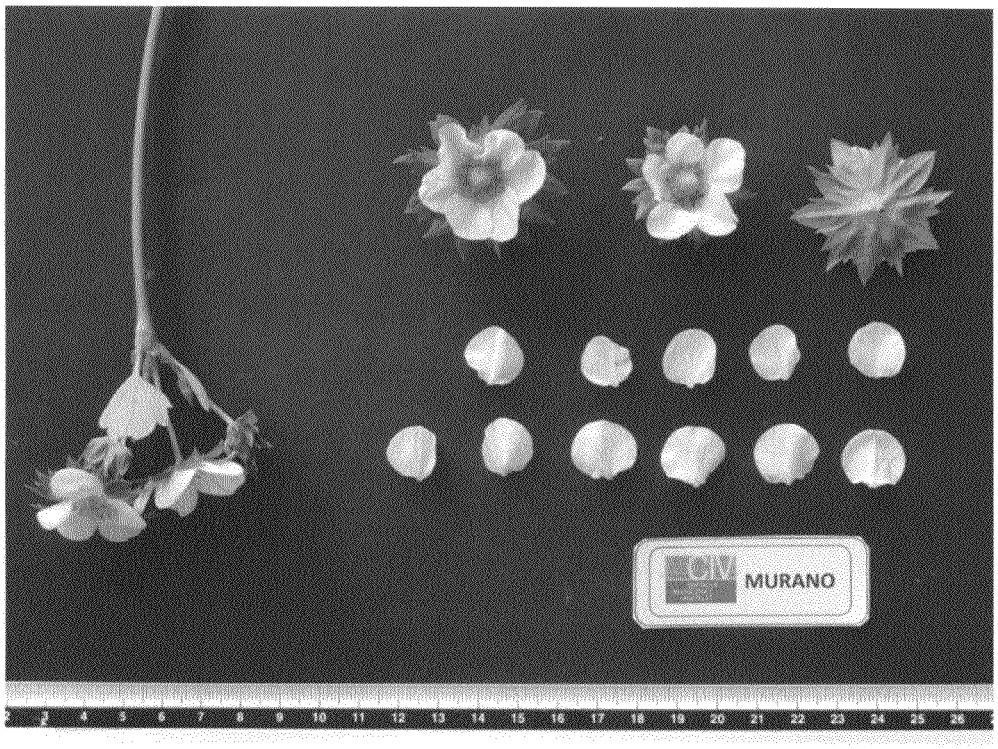
FIG. 3 shows the flowers of 'MURANO'.
Figure 4:
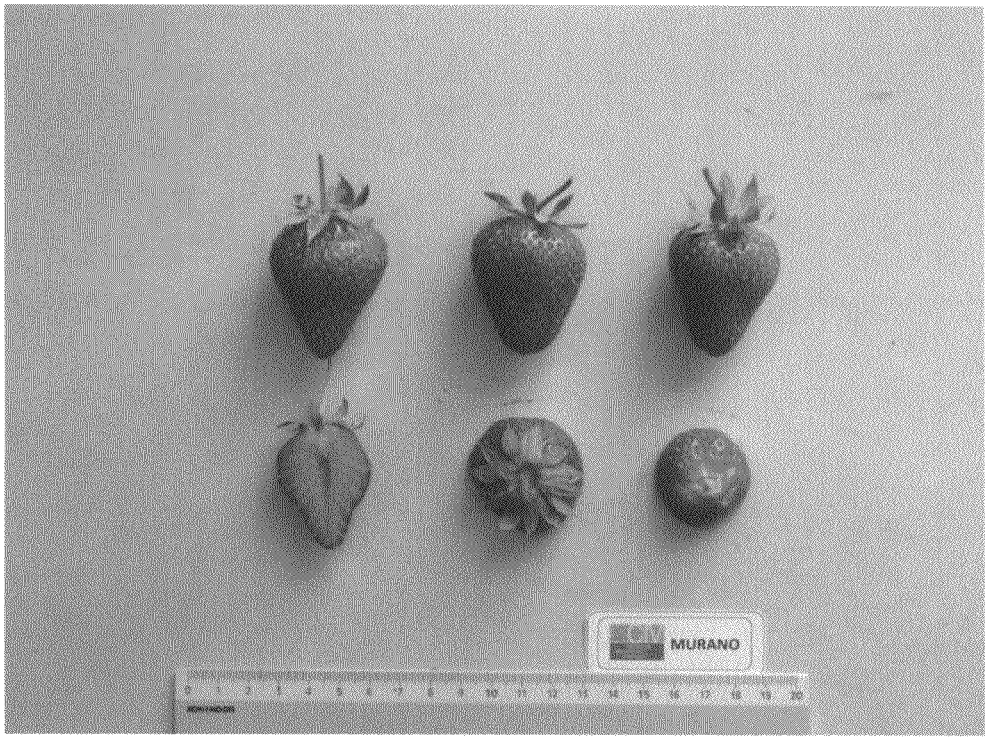
FIG. 4 shows the fruits of 'MURANO'.

The colors of this illustration may vary with lighting conditions and, therefore, color characteristics of this new variety should be determined with reference to the observations described herein, rather than from these illustrations alone.

DETAILED BOTANICAL DESCRIPTION

The following detailed description of the 'MURANO' variety, unless otherwise noted, is based on observations taken of plants and fruits, and asexually reproduced progeny, grown at S. Giuseppe di Comacchio, Ferrara, Italy.

The observed plants were one year old plants, produced in a nursery in S. Giuseppe di Comacchio, Italy, dug in December, cold stored, and then planted in production fields in the middle of April.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. Color designations are made with reference to The Royal Horticultural Society (R.H.S.) Colour Chart.

Plant:

*Habit*.—Semi-upright.
*Density*.—Medium.
*Vigor*.—Medium High.
*Overall shape*.—Slightly Upright.
*Height*.—About 0.30 meters.
*Width*.—About 0.45 meters.

Leaf:

*Color*.—Upperside: RHS 137A green group; underside: RHS 138B green group.
*Size*.—Medium.
*Cross section*.—Concave.
*Leaf surface undulation or blistering*.—Medium.
*Number of leaflets*.—Three only.
*Leaf stem characteristics*.—Color: RHS 145A yellow-green group. Position of hairs: upwards. Length: About 13 cm.
*Terminal leaflet*.—Length/width ratio: Moderately longer. Length: About 10 cm. Width: About 8 cm. Shape of base: Obtuse. Shape of teeth: Serrate to crenate.
*Petiole*.—Position of hairs: Slightly outwards. Length: About 13 cm.
*Stipule*.—Color RHS 145A yellow-green group. Anthocyanin coloration: absent to very weak.
*Stolons*.—Number about 6-7. Thickness: Medium, average 3.66 mm. Pubescence: Sparse. Color RHS 145A, yellow green with weak anthocyanin coloration, RHS 186B greyed-purple.

Inflorescence: Position relative to foliage: Same level.

*Flower*.—Size: Medium. Size of calyx relative to corolla: Same size. Spacing of petals. touching.
*Flower characteristics*.—Diameter primary flowers. About 3.7 cm. Diameter secondary flowers. About 2.5-3.0 cm. Number of petals: normally 5 to 6. Fragrance: No significant fragrance. Time from bloom to mature fruit: About 28-32 days.

Reproductive organs:

*Stamens*.—Numerous with pollen present, fertile and abundant. Length: approximately 2.5 mm. Color: near RHS 145C yellow-green.
*Anthers*.—Size: Generally average, length: about 1.3 mm; width: about 0.9 mm. Color: RHS 17C yellow orange; darkening with advanced maturity.
*Pollen*.—Fertile and abundant. Color: RHS 14A yellow orange.
*Pistils*.—Numerous, generally average in size. Color: RHS 151C yellow-green.
*Petal*.—Length/width ratio: equal.

Fruit:

*Fruit truss*.—Attitude: Erect.
*Ratio of length/maximum width*.—Moderately longer.
*Color of mature fruit*.—RHS 45A red.
*Color of internal fruit*.—RHS 44B red.
*Length*.—40.5-43 mm.
*Width*.—33-35 mm.
*Calyx diameter*.—32-34 mm.
*Average weight*.—18-20 grams.
*Achene color*.—RHS 153C yellow-green.
*Number of achenes per cm*$^2$.—About 9.9.
*Achene size*.—Length about 1.5 mm, width about 1.1 mm.
*Weight of* 1000 *achenes*.—0.72 grams.
*Peduncle length of inflorescence stem*.—Primary fruit about 3 to 5 cm, secondary fruit about 2 to 3 cm, color near RHS 138A green.
*Marketable yield* (*gm/plant*).—About 900-1100 grams.
*Fruit size*.—Large.
*Predominant shape*.—Conical.
*Difference in shapes between primary and secondary fruit*.—None or very slight.
*Band without achenes*.—Absent to very narrow.
*Unevenness of surface*.—Even to very slightly uneven.
*Evenness of color*.—Even to very slightly uneven.
*Glossiness*.—Medium.
*Insertion of achenes*.—Below surface.
*Insertion of calyx*.—Level with fruit.
*Attitude of the calyx*.—Outwards or slightly upwards.
*Size of calyx in relation to fruit diameter*.—Same size.
*Adherence of calyx*.—Strong.
*Firmness of flesh*.—Firm.
*Hollow center expression*.—Medium.
*Flavor*.—Good.
*Soluble solids* (% *brix*).—Average 9°.
*Time of first flowering*.—About 25-30 days after planting using cold stored plants quality A.
*Time of first harvesting*.—About 28-32 days after first flowering.
*Harvest period*.—June to November.
*Type of bearing*.—Fully remontant.

Disease resistance: The 'MURANO' variety has been tested for several years and it has manifest good vigor and good tolerance to diseases. No specific resistance assessment has been done.

What is claimed is:

1. A new and distinct variety of *Fragaria Ananassa×Duch*. plant named 'MURANO', as illustrated and described herein.

* * * * *